United States Patent [19]

Clavin

[11] 4,432,347

[45] Feb. 21, 1984

[54] COSMETIC TAPE AND METHOD

[76] Inventor: Harold D. Clavin, 2001 Santa Monica Blvd., Suite 890-West, Santa Monica, Calif. 90404

[21] Appl. No.: 440,846

[22] Filed: Nov. 12, 1982

[51] Int. Cl.³ .............................................. A61B 17/00
[52] U.S. Cl. .................................... 128/1 R; 128/20; 128/163
[58] Field of Search .................. 128/163, 1 R, 20, 1.3

[56] References Cited

U.S. PATENT DOCUMENTS

| | | | |
|---|---|---|---|
| 1,970,086 | 8/1934 | Frost | 128/163 |
| 2,572,638 | 10/1951 | Loos | 128/163 |
| 3,626,940 | 12/1971 | Zaffaroni | 128/1.3 X |
| 4,134,401 | 1/1979 | Galacian | 128/163 |

FOREIGN PATENT DOCUMENTS

| | | | |
|---|---|---|---|
| 2401654 | 2/1977 | France | 128/1 R |
| 2400353 | 8/1977 | France | 128/1 R |
| 491378 | 2/1973 | U.S.S.R. | 128/1 R |
| 197706 | 6/1977 | U.S.S.R. | 128/1 R |
| 648222 | 2/1979 | U.S.S.R. | 128/1 R |

*Primary Examiner*—George F. Lesmes
*Assistant Examiner*—Swisher, Nancy A. B.
*Attorney, Agent, or Firm*—Poms, Smith, Lande & Rose

[57] ABSTRACT

An adhesive tape and method for use thereof in non-surgically taking a tuck in loose skin such as that comprising the upper eyelid. When applied to a drooping upper eyelid by stretching the skin of the eyelid away from the ciliary margin, applying the tape to the eyelid, and then folding the skin of the upper eyelid down to be attached to the other side of the tape and then back upon itself, a pseudo upper blepharoplasty is effected, which can be left in place for extended periods of time, thus avoiding surgery. The adhesive strip has a backing and adhesive such as to make the strip very thin, very soft and pliable, strong, tear resistant, easily conformed to body contours, non-irritating and water resistant.

4 Claims, 15 Drawing Figures

Fig. 1.
Fig. 2.
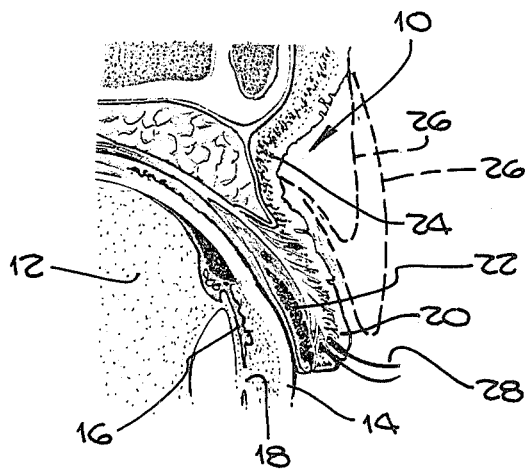
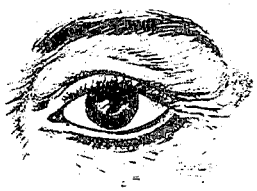
Fig. 4. PRIOR ART
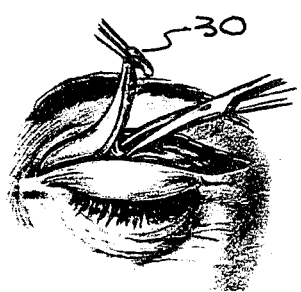
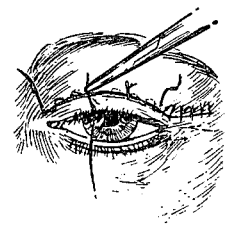
Fig. 3. PRIOR ART
Fig. 5.
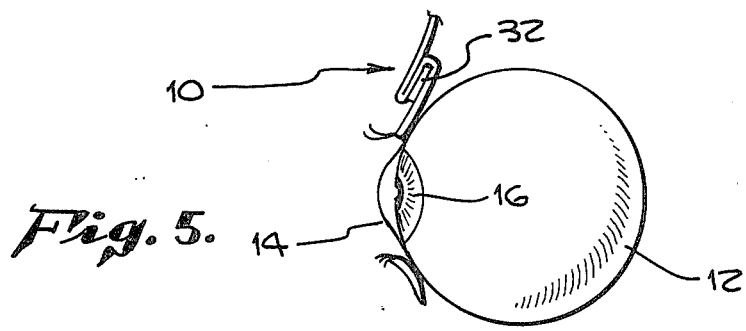

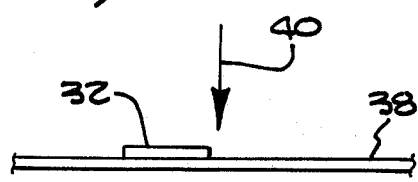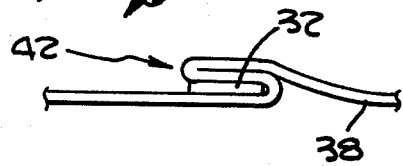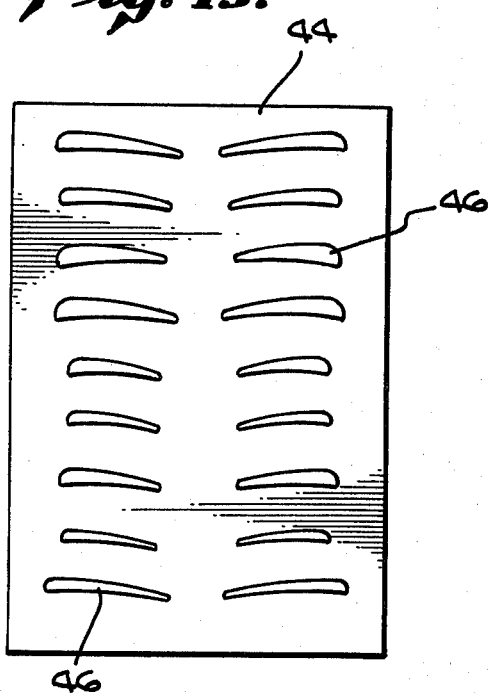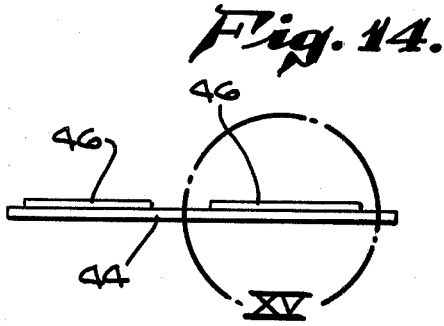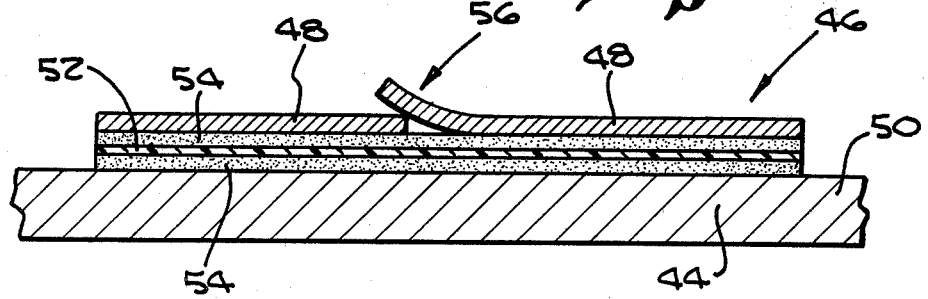

COSMETIC TAPE AND METHOD

BACKGROUND OF THE INVENTION

The present invention relates to tapes and adhesives and, more particularly, to adhesive tape used for cosmetic purposes.

A cutaway drawing through the upper eyelid is shown in FIG. 1. The upper eyelid, generally indicated as 10, moves down over the eyeball 12 when the eyes are closed, and retracts over the cornea 14 to expose the iris 16 and pupilary opening 18 when the eye is open. The skin of the upper eyelid 10 along the ciliary margin 20 is held relatively rigid by a thin strip of cartilage known as the tarsal plate 22. The skin above the ciliary margin 20 is thin and supple and tends to fold at what is referred to as the supra tarsal fold 24.

Particularly as part of the natural aging process, the skin of the upper eyelid can sag or droop into positions such as those shown ghosted and labelled 26 in FIG. 1. The result is a bagging or festooning of the upper eyelid as shown in FIG. 2. A similar condition occurs naturally in the eyes of many persons of Oriental extraction due to a difference in eye physiology.

When the natural or developed droop reaches the lower ghosted position 26 of FIG. 1 adjacent the eyelashes 28, several things can happen. First, the actual vision above the horizontal can be affected. That is, merely rotating the eyeball 12 in an upward direction does not provide a view in that direction since the line of vision is covered by the drooped portion 26 of the eyelid 10. Even without the reduced vision, the natural puffiness and droop in the non-Oriental eye tends to make the associated eye (and, therefore, the person) look older. Additionally, in women, it can interfere with the application of eye makeup.

Statistically, there are at least 44 million women over the age of 40 in the United States alone. It can be assumed that a drooping condition such as that shown in FIG. 2 is of some bother to at least a substantial portion of them. The condition can be corrected surgically in the manner shown in FIGS. 3 and 4. And, in fact, several hundred thousand people a year have the procedure shown therein performed to alleviate the condition. As shown in FIG. 3, a strip 30 of the upper eyelid 10 is surgically removed along with some of the fat beneath the strip 30. The sides of the wound are then sutured together as shown in FIG. 4, thus removing a portion of the excess skin above the upper eyelid 10 thereby removing the droop as shown in FIG. 2. Such a procedure is referred to as an upper blepharoplasty.

The above-described procedure is neither inconsequential nor inexpensive. For most of the persons afflicted with drooping eyes such as that shown in FIG. 2, the condition remains one of annoyance either due to lack of funds for the surgery or a lack of desire or willingness to have the surgery itself.

Wherefore, it is the object of the present invention to provide a method and apparatus for providing a non-surgical method for affecting a temporary pseudo upper blepharoplasty.

SUMMARY

The foregoing objective has been accomplished by the method of the present invention comprising the steps of stretching the skin of the upper eyelid upward away from the ciliary margin thereby unfolding the natural super tarsal fold; while the skin is stretched, attaching one side of a narrow, curved, adhesive strip having adhesive on both sides to the skin of the upper eyelid and extending substantially between the medial and lateral canthi with its bottom edge spaced above the ciliary margin about 8-12 mm and/or with its top edge above the inner fold line of the natural supra tarsal fold, the strip having a backing and adhesive being such as to make the strip very thin, very soft and pliable, strong, tear resistant, easily conformed to body contours, non-irritating, and water resistant; folding the skin of the upper eyelid down over the adhesive strip and attaching it to the exposed adhesive on the other side of the adhesive strip; and, folding the folded skin of the upper eyelid back upon itself with its edge along the bottom edge of the adhesive strip to form an artificial supra tarsal fold which is deeper and higher than the material natural fold.

DESCRIPTION OF THE DRAWINGS

FIG. 1 is a detailed cutaway drawing of a side view of an upper eyelid.

FIG. 2 is a front view of a left eye having a bagged or festooned upper eyelid.

FIGS. 3 and 4 show the steps of the prior art surgical technique of blepharoplasty used to correct the condition of FIG. 2.

FIG. 5 is a simplified drawing of a side view through an eyeball and the eyelids showing the non-surgical technique of the present invention for forming a temporary pseudo upper blepharoplasty.

FIGS. 10-12 are simplified drawings through a segment of loose skin showing the general technique and method of the present invention for producing a non-surgical tuck in the skin.

FIG. 13 is a plan view of the adhesive strips of the present invention in their preferred embodiment.

FIG. 14 is an end view of FIG. 13.

FIG. 15 is an enlarged cutaway view of FIG. 14 in the area designated by XV.

DESCRIPTION OF THE PREFERRED EMBODIMENT

Figure 6:
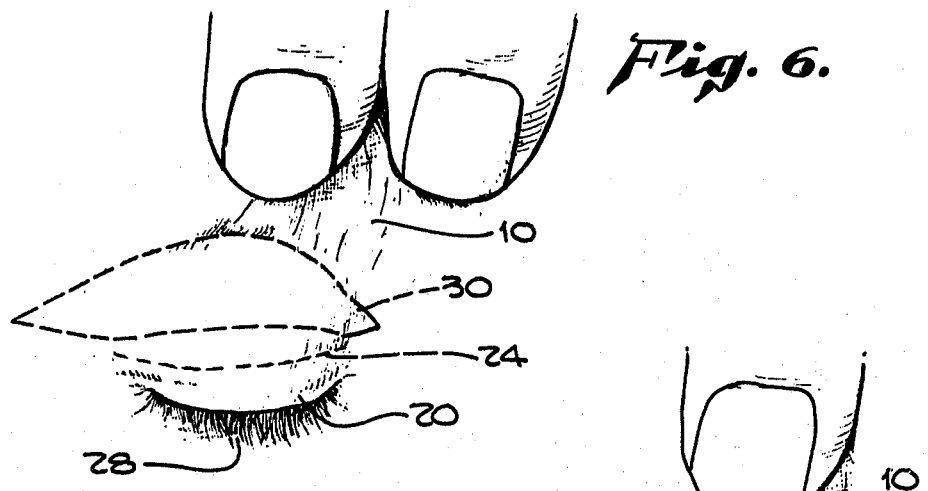
FIGS. 6-8 show the steps of performing the method of present invention to accomplish the result of FIG. 5. A right eye being shown.

The description which follows hereinafter is with respect to the method and apparatus of the present invention as applied to providing a temporary pseudo upper blepharoplasty. It should be recognized that the technique and materials shown can also be used for any application where it is desired to take a non-surgical tuck in loose skin. Thus, it is envisioned that the technique and materials discussed herein can be used, for example, by plastic and reconstructive surgeons for demonstrating to potential patients an approximation of the effect which will be obtained by surgery as well as by theatre makeup artists and the like in producing desired temporary visual effects.

Turning first to FIG. 5, a simplified drawing through the upper eyelid 10 in conjunction with an eyeball 12 is shown, depicting the desired objective of the present invention; that is, if the natural supra tarsal fold in the upper eyelid 10 is replaced by a deeper artificial supra tarsal fold, an effective tuck will be taken in the loose skin of the upper eyelid 10. According to the present invention, a very thin strip of double-sided adhesive tape 32 generally less than 1 cm in width and 4 cm in length is attached to the upper eyelid 10 with the bottom edge spaced about 8-12 mm above the ciliary margin 20 and/or the top edge above the fold line of the natural supra tarsal fold. The skin above the adhesive strip 32 is then folded down and then back upon itself as shown in FIG. 5 with the bottom edge of the skin aligned along the bottom edge of the tape 32. Th adhesive strip 32 maintains the deeper and higher artificial supra tarsal fold thus formed in the desired position.

Figure 7:
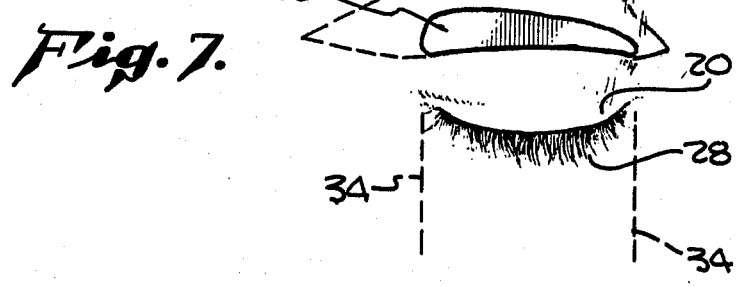
Figure 8:
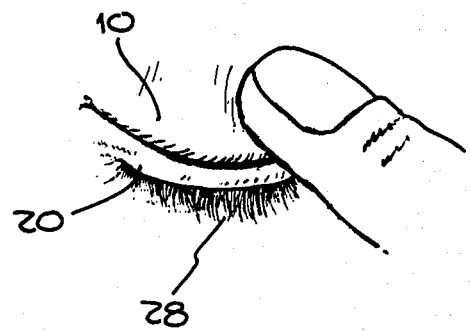

Turning now to FIGS. 6 through 8, the technique is shown in greater detail. In FIG. 6, with the eye closed, the skin of the upper eyelid 10 is stretched away from the ciliary margin 20 thus unfolding the natural supra tarsal fold, which is indicated by the dashed line labelled 24. The area which would normally be removed in an actual surgical blepharoplasty is indicated by the dotted line 30 for reference. For purposes of understanding, the eye shown in FIGS. 6-8 is a right eye such that the medial canthus is to the viewer's right and the lateral canthus is to the viewer's left. With the skin stretched as in FIG. 6, a curved double-sided adhesive strip 32 is attached on its one side to the skin on the upper eyelid 10 as shown in FIG. 7. From repeated test applications, it has been determined that the sizing and configuration shown in FIG. 7 produces the best results. The strip 32 can be positioned easily in either, or both, of two ways; with the bottom edge spaced from the ciliary margin 20 a given distance such as, for example, 8 to 12 mm and/or with the top edge of the tape 32 above the natural supra tarsal fold line 24. The adhesive strip 32 in its preferred embodiment is curved along the natural line of the ciliary margin 20 when the eye is opened. It is sized in length to fit between the two canthi as indicated by the two vertical dotted lines 34. In the average eye this distance is approximately 33 millimeters, such that a length for the adhesive strip 32 in that approximate amount is preferable. A maximum width of the strip 32 of approximately 5 millimeters has been found to give preferable results with a slight tapering towards the medial canthis.

Figure 9:
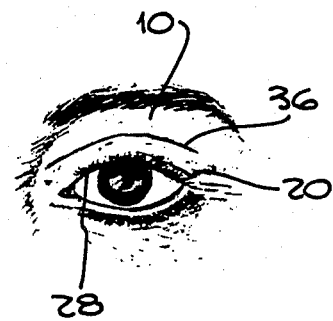
FIG. 9 is a drawing showing a left eye following the procedures of FIGS. 6-8.

With the adhesive strip 32 in place, the skin of the upper eyelid 10 is pulled gently down over the adhesive strip 32 and evenly attached thereto aligned with the bottom edge, after which it is folded back upon itself. This is shown in FIG. 8. This results in a thin tuck line at 36 which is raised and evenly spaced from the ciliary margin 20. As can be seen in FIG. 9, the result is an eye with reduced bagging of the upper eyelid 10 and with a uniform distance between the tuck line 36 and the ciliary margin 20. The artificial supra tarsal fold thus created is deeper and higher and takes up a portion of the undesired skin of the upper eyelid 10. It has been found that after a period of wearing the adhesive strip 32 as thus positioned, once it is removed, the artificial supra tarsal fold remains for a period of time without the necessity of the adhesive strip 32.

The general technique of the present invention with respect to taking a non-surgical tuck in any loose skin is shown in simplified form in FIGS. 10-12. Assume that it is desired to take a tuck in the skin 38 along a line as indicated by the arrow 40. The tuckline 40 can be straight or curved, as desired. A double-sided adhesive strip 32 of a type to be described in greater detail hereinafter is attached along one of its adhesive surfaces to the skin 38 adjacent the intended tuck line 40. The skin on the other side of the tuck line 40, generally indicated as 42, is folded over the adhesive strip 32 to adhere to the exposed adhesive surface thereof. Fold skin 42 is then folded back upon itself as shown in FIG. 12 to create the desired tuck in the skin.

The adhesive strip of the present invention in its preferred embodiment will now be discussed in greater detail. Turning to FIGS. 13 and 14, the preferred embodiment of the present invention for use in practicing the method of pseudo blepharoplasty is shown. A release surfaced liner sheet 44 has a plurality of pre-formed adhesive strips 46 including a peel-off liner 48 attached thereto. The construction of each strip 46 is shown in greater detail at FIG. 15. The liner sheet 44 is preferably of a heavier paper or cardboard with a suitable surface at 50 to allow the pre-formed strips 46 to be easily removed therefrom without reducing their adhesive qualities. Each pre-formed strip 46 comprises a extremely thin backing 52 having adhesive 54 attached to either side thereof, and with a split, peel-off liner 48 on the outer surface. The peel-off liner 48 is preferably of a type which is split in the middle with an overlap as at 56. This allows the liner 48 to be easily removed from the outer adhesive 54 when the strip 46 is attached to the skin of the upper eyelid 10 by the opposite adhesive surface. To properly achieve the objectives of the present invention, the backing 52 and adhesive 54 must be chosen such as to make the strip very thin, very soft and pliable, strong, tear resistant, easily conformed to body contours, non-irritating, and water resistant. It is preferred that the backing 52 be of a porous material such that the skin of the upper eyelid 10 can breathe so that the strip can be left in position for a longer period of time. The applicant herein found that an appropriate backing and adhesive combination can be obtained from the Minnesota, Mining and Manufacturing Company (3M Company) of St. Paul, Minn.

Optionally, the liner 48 can be pre-marked with curved strip patterns to be hand out and/or modified, or be made with a surface for tracing patterns upon at time of use for cutting and/or modifying.

Thus, from the foregoing description, it can be seen that the method and material of the present invention allows a non-surgical tuck to be taken in loose skin in general and, more particularly, in the upper eyelid to accomplish a temporary pseudo upper blepharoplasty.

Wherefore, having thus described my invention, I claim:

1. A method for non-surgically taking a tuck in loose skin in an eyelid comprising the steps of:
  (a) attaching one side of an adhesive strip having adhesive on both sides along one side of the intended tuck area; and
  (b) folding the skin of the intended tuck that is not yet adheased over the adhesive strip and attaching it to the exposed adhesive on the other side of the adhesive strip.

2. A non-surgical method for effecting a temporary pseudo upper blepharoplasty comprising the steps of:
  (a) stretching the skin of the upper eyelid upward away from the ciliary margin thereby unfolding the natural super tarsal fold;
  (b) while the skin is stretched, attaching one side of an adhesive strip having adhesive on both sides to the skin of the upper eyelid and extending generally between the medial and lateral canthi with its bottom edge spaced from the ciliary margin;
  (c) folding the skin of the upper eyelid over the adhesive strip and attaching it to the exposed adhesive on the other side of the adhesive strip; and, (d) releasing the skin of the upper eyelid to allow it to relax once all adhesions have taken place, and form an artificial supra tarsal fold which is higher than the natural fold and raises the redundant skin away from the ciliary margin.

3. The method of claim 2 wherein:
the bottom edge of the adhesive strip is disposed at a distance of about 8 mm to 12 mm from the ciliary margin.

4. The method of claim 2 wherein:
in said step (c) thereof, the folded skin is attached to the bottom of the adhesive strip and folded back with its edge along the bottom edge of the adhesive strip.

* * * * *